(12) United States Patent
Frey et al.

(10) Patent No.: US 11,362,285 B2
(45) Date of Patent: *Jun. 14, 2022

(54) SEMICONDUCTING MATERIAL AND NAPHTHOFURANE MATRIX COMPOUND FOR IT

(71) Applicant: Novaled GmbH, Dresden (DE)

(72) Inventors: Julien Frey, Dresden (DE); Annette Steudel, Dresden (DE)

(73) Assignee: Novaled GmbH, Dresden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,930

(22) Filed: May 14, 2020

(65) Prior Publication Data

US 2020/0280002 A1    Sep. 3, 2020

Related U.S. Application Data

(63) Continuation of application No. 15/552,133, filed as application No. PCT/EP2016/053454 on Feb. 18, 2016, now Pat. No. 10,658,599.

(30) Foreign Application Priority Data

Feb. 18, 2015 (EP) ..................................... 15155603
Apr. 8, 2015 (EP) ..................................... 15162788

(51) Int. Cl.
    *H01L 51/00*      (2006.01)
    *C07D 405/14*      (2006.01)
    (Continued)

(52) U.S. Cl.
    CPC ........ *H01L 51/0073* (2013.01); *C07D 405/14* (2013.01); *C07F 9/6561* (2013.01); *H01L 51/0067* (2013.01); *H01L 51/0072* (2013.01); *H01L 51/001* (2013.01); *H01L 51/002* (2013.01); *H01L 51/5072* (2013.01); *H01L 51/5076* (2013.01); *H01L 51/5092* (2013.01)

(58) Field of Classification Search
    CPC .................................................. H01L 51/0073
    See application file for complete search history.

(56) References Cited

U.S. PATENT DOCUMENTS 9,028,977 B2    5/2015   Bae et al.
9,484,540 B2    11/2016   Ito et al.
(Continued)

FOREIGN PATENT DOCUMENTS

EP      2818464 A1    12/2014
JP      2009-215425 A    9/2009

OTHER PUBLICATIONS

PCT International Search Report and Written Opinion for PCT Application No. PCT/EP2016/053454 dated May 18, 2016 (8 pages).

(Continued)

*Primary Examiner* — Peter F Godenschwager
(74) *Attorney, Agent, or Firm* — Eversheds Sutherland (US) LLP

(57) ABSTRACT

The present invention relates to a semiconducting material comprising an electron transport matrix compound comprising at least one electron transporting structural moiety and at least one polar structural moiety; a matrix compound and electronic device utilizing the semiconducting material.

9 Claims, 1 Drawing Sheet

(51) Int. Cl.
    *C07F 9/6561*         (2006.01)
    *H01L 51/50*         (2006.01)

(56) References Cited

U.S. PATENT DOCUMENTS

| | | |
|---|---|---|
| 10,658,599 B2 * | 5/2020 | Frey .................... C07F 9/6561 |
| 2014/0183500 A1 | 7/2014 | Ikeda et al. |
| 2014/0291654 A1 | 10/2014 | Kim et al. |
| 2015/0243895 A1 | 8/2015 | Lim et al. |
| 2015/0243908 A1 * | 8/2015 | Lee .................... C07D 405/10 257/40 |
| 2016/0285011 A1 | 9/2016 | Park et al. |

OTHER PUBLICATIONS

EP Search Report for EP Application No. 15155603 dated Aug. 5, 2015 (4 pages).
Jeong et al., "Dibenzofuran Derivative as High Triplet Energy Host Material for High Efficiency in Deep Blue Phosphorescent Organic Light-Emitting Diodes," Organic Electronics, 2012, 13:1141-1145.
Chinese Office Action for CN Application No. 201680010833.3 dated Oct. 31, 2018 (10 pages) (English translation).
Taiwanese Examination Notification for TW Application No. 105104596 dated Aug. 19, 2019 (4 pages) {English translation).
Japanese Office Action for JP Application No. 2017-542908 dated Feb. 4, 2020 (4 pages) (English translation).
Examination Notification in Taiwan Patent Application No. 105104596 (English translation), completed Feb. 24, 2020.

* cited by examiner

SEMICONDUCTING MATERIAL AND NAPHTHOFURANE MATRIX COMPOUND FOR IT

CROSS REFERENCE TO RELATED APPLICATIONS

This application is a continuation of U.S. patent application Ser. No. 15/552,133, filed Aug. 18, 2017, which is a U.S. national stage application of PCT/EP2016/053454, filed Feb. 18, 2016, which claims priority to European Application Nos. 15155603.2 and 15162788.2, filed Feb. 18, 2015 and Apr. 8, 2015, respectively. The contents of these applications are hereby incorporated by reference.

FIELD OF THE INVENTION

The present invention concerns organic semiconducting material with improved electrical properties, matrix compound suitable for this organic semiconducting material and electronic device utilizing the improved electrical properties of the inventive semiconducting material.

BACKGROUND OF THE INVENTION

Among the electronic devices comprising at least a part based on material provided by organic chemistry, organic light emitting diodes (OLEDs) have a prominent position. Since the demonstration of efficient OLEDs by Tang et al. in 1987 (C. W. Tang et al., Appl. Phys. Lett. 51 (12), 913 (1987)), OLEDs developed from promising candidates to high-end commercial displays. An OLED comprises a sequence of thin layers substantially made of organic materials. The layers typically have a thickness in the range of 1 nm to 5 μm. The layers are usually formed either by means of vacuum deposition or from a solution, for example by means of spin coating or jet printing.

OLEDs emit light after the injection of charge carriers in the form of electrons from the cathode and in form of holes from the anode into organic layers arranged in between. The charge carrier injection is effected on the basis of an applied external voltage, the subsequent formation of excitons in a light emitting zone and the radiative recombination of those excitons. At least one of the electrodes is transparent or semitransparent, in the majority of cases in the form of a transparent oxide, such as indium tin oxide (ITO), or a thin metal layer.

It is an objective of the invention to overcome the drawbacks of the prior art and to provide alternative compounds which can be successfully used as semiconducting materials and, especially, as charge transport matrix compounds in electrically doped semiconducting materials for use in electronic devices, particularly in OLEDs.

SUMMARY OF THE INVENTION

The objective is achieved by a semiconducting material comprising
  an electron transport matrix compound comprising at least one electron transporting structural moiety and at least one polar structural moiety, the at least one polar structural moiety being selected from
  a) a structural moiety consisting of one atom of 15$^{th}$ group of the Periodic Table and one atom of 16$^{th}$ group of the Periodic Table linked together by a covalent bond, or
  b) from a heteroaryl selected from pyridine-2-yl, pyridine-4-yl, quinoline-4-yl and 1,3,5-triazine-2-yl, or
  c) from a benzimidazolyl moiety having formula (Ia) or (Ib)

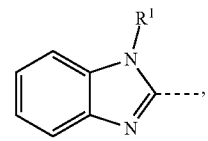

(Ia)

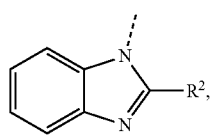

(Ib)

wherein the dashed line represents the bond attaching the benzimidazolyl moiety of formula (Ia) or (Ib) to other structural moieties of the molecule, $R^1$ and $R^2$ are selected from
(i) $C_1$-$C_{24}$ alkyl,
(ii) $C_3$-$C_{24}$ cycloalkyl,
(iii) $C_6$-$C_{24}$ aryl,
(iv) $C_7$-$C_{24}$ arylalkyl,
(v) $C_3$-$C_{24}$ heteroalkyl or $C_4$-$C_{24}$ heterocycloalkyl or $C_8$-$C_{24}$ aryl-heteroalkyl each comprising at least one heteroatom selected from Si and Ge,
(vi) $C_2$-$C_{24}$ heteroalkyl or $C_3$-$C_{24}$ heterocycloalkyl or $C_7$-$C_{24}$ aryl-heteroalkyl each comprising at least one heteroatom selected from B and P, and from
(vii) $C_2$-$C_{24}$ heteroaryl comprising up to 4 heteroatoms independently selected from N, O and S; wherein
the at least one electron transporting structural moiety comprises a benzo-naphtofurane structural moiety, with the proviso that the case that the benzo-naphtofurane structural moiety has the structure (IIa)

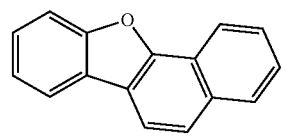

(IIa)

and the polar structural moiety has the structure (Ib) is excluded.

The benzo-naphtofurane structural moiety and the polar structural moiety may be directly linked by a covalent bond or may be separated from each other by a linker structural moiety. In one of preferred embodiments, the linker structural moiety is a sterically rigid group. Typical examples of sterically rigid groups are polycyclic aliphatic or heteroaliphatic structural moieties, for example an adamantane or a norbornane structural moiety. Another example of sterically rigid moieties are aromatic or heteroaromatic moieties, which may be either monocyclic or polycyclic. A specific example of polycyclic aromatic or heteroaromatic structural moieties are condensed polycyclic aromatic or heteroaromatic structural moieties.

The linker moiety may further allow a conjugation of delocalized electrons between the benzo-naphtofurane electron transporting structural moiety and the polar structural moiety. In one of preferred embodiments, the linker between the benzo-naphtofurane structural moiety and the polar structural moiety is an arylene or heteroarylene linker. Preferably, the arylene linker or the heteroarylene linker comprises up to three aromatic rings and/or up to 24 carbon atoms. A preferred example of the arylene linker is a phenylene. The arylene and heteroarylene linkers are both sterically rigid and allowing the conjugation of delocalized electrons between the benzo-naphtofurane electron transporting structural moiety and the polar structural moiety.

The phenylene may be selected from ortho-, meta- and para-phenylene. For sterical reasons, m- and p-phenylene linkers are preferred.

The benzo-naphtofurane structural moiety is preferably a dinaphtofurane structural moiety. In a more preferred embodiment, the dinaphtofurane structural moiety has the structure according to formula (II)

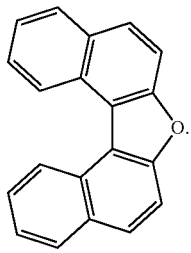

(II)

Also preferably, the polar structural moiety or the linker bearing the polar structural moiety is attached to the benzonaphtofurane structural moiety in the position of the benzonaphtofurane structural moiety which is next (closest) to the oxygen heteroatom of the benzonaphtofurane structural moiety.

A typical polar structural moiety consisting of one atom of $15^{th}$ group of the Periodic Table and one atom of $16^{th}$ group of the Periodic Table linked together by a covalent bond is the phosphine oxide group. Preferably, the structural moieties directly attached to the phosphine oxide group are arene or heteroarene structural moieties. Examples of arene structural moieties are aryl or arylene groups, examples of heteroarene structural moieties are heteroaryl or heteroarylene groups. In one embodiment of the invention, the polar structural moiety consists of one atom of $15^{th}$ group of the Periodic Table and one atom of $16^{th}$ group of the Periodic Table linked together by a covalent bond and its atom of $15^{th}$ group of the Periodic Table is member of a covalent ring structure. An example of such polar structural moiety attached to covalent ring structure can be a phosphine oxide group substituted with at least two structural units selected from arylene and heteroarylene, wherein the at least two structural units are linked together to form a ring.

If not explicitly stated that a group or structural unit is unsubstituted, the structural unit may be substituted and the count of atoms (e.g., count of carbon atoms) given for it then comprises also possible substituents. The number of carbon atoms or heteroatoms comprised in the matrix compound of the semiconducting material according to invention is not specifically limited. Should the semiconducting material be processed by vacuum thermal evaporation (VTE), it is advantageous that the relative molecular weight of the comprised electron transport matrix compound is roughly in the range 200-1200, preferably in the range 300-1000, more preferably in the range 400-900, even more preferably in the range 500-800.

It is desirable that the size of the polar structural moiety, of the optional linker between the polar structural moiety and the benzo-naphtofurane structural moiety, and the number and the size of the substituents tuning the properties of the electron transport matrix compound of the semiconducting material according to the invention are commensurate to the number and size of benzo-naphtofurane structural moieties comprised in the molecule of the electron transport matrix compound. It is preferred that the benzo-naphtofurane structural moieties comprise not less than 20% of the overall count of carbon atoms in the electron transport matrix compound, more preferably not less than 30% of the overall count of carbon atoms, even more preferably not less than 40% and most preferably not less than 50% of the overall count of carbon atoms in the electron transport matrix compound.

Preferred substituents are structural moieties which are thermally and chemically stable. The term "chemical stability" is used in the sense that stable groups do not exhibit, under conditions of use in the semiconducting material, a detectable reactivity with auxiliary compounds (for example with typical electrical dopants that serve for improving electrical properties of doped semiconducting materials) or with ambient conditions (e.g. a reactivity with moisture or a light-induced reactivity). Substituents may serve for tuning the processability or electronic properties of the semiconducting material.

Examples of stable electron donating substituents are alkyl, alkylene, heteroalkyl or heteroalkylene structural moieties, like methyl group, methoxy group, ethyl group, ethoxy group, methylenedioxy group, alkylthio group, and five-membered heterocyclic structural moieties comprising up to three heteroatoms selected from N, O and S. Examples of sufficiently stable electron withdrawing structural moieties are halogen atoms, halogenated or perhalogenated alkyl groups, six-membered nitrogen-containing heteroaryl or heteroarylene moieties like pyridyl, diazinyl, triazinyl, bis (pyridine)-diyl, phenanthrene-diyl, halogenated or perhalogenated aryl groups, halogenated or perhalogenated arylene groups, halogenated or perhalogenated heteroaryl groups, halogenated or perhalogenated heteroarylene groups, nitrile groups, nitro groups, electron withdrawing heteroaryls.

The skilled person can combine the electron withdrawing or electron donating groups appropriately to arrive at desired frontier orbital energy level, fitting with the purpose of the semiconducting material in the device and with energy levels of auxiliary compounds which may be added to form a mixed (doped) semiconducting material or which are used in layers adjacent to the layer comprising the semiconducting material according to this invention.

For example, it is well-known that electron withdrawing strength of a substituted or unsubstituted aryl, arylene, heteroaryl or heteroarylene structural moiety may be augmented by its substitution with nitrile groups, acyl groups, aryl groups, arylsulfonyl groups and other electron withdrawing groups, whereas the substitution with electron donating groups will decrease the electron withdrawing strength of the same structural moiety.

More specifically, the localization of a frontier orbital like LUMO in the molecule can be assigned by a skilled person to that part of the molecule which contains the largest conjugated pi-electron system. It is preferred that the LUMO of the electron transport matrix compound of the semiconducting material according this invention is localized mostly on its benzonaphtofurane structural moiety. In case that two or more pi-electron systems with the same extent (given by the number of pi electrons in conjugation) occur in the molecule, the lowest frontier orbital energy can be assigned to the system linked with strongest electron withdrawing groups and/or weakest electron donating groups. The electron withdrawing and/or electron accepting effects of various substituents are commensurate to experimentally accessible parameters like Hammet or Taft constants which are tabulated for large number of substituents most frequently occurring in aromatic or heteroaromatic organic compounds. In most cases, the above mentioned parameters are sufficient for a reliable LUMO localization, because the overall effect of more substituents attached to the same aromatic system is additive. In case of uncertainty, the ultimate method for the correct LUMO localization in the molecule is quantum chemical calculation. Reliable results with relatively low demand for computational capacity provide for example the methods based on density functional theory (DFT).

It is desirable that the LUMO energy level in the electron transport matrix compound of the semiconducting material according this invention, measured as a redox potential by cyclic voltammetry (CV) in tetrahydrofuran (THF) against ferrocenium/ferrocene redox couple as a reference, is in the range −1.8--−3.1 V. It is preferred that the energy of this LUMO is in the range −2.0--−2.9 V, more preferably in the range −2.15--−2.75 V, even more preferably in the range −2.25--−2.6 V. Modern quantum chemical methods allow also a reliable estimation of relative LUMO energies for different molecules. The computed relative values can be recalculated to absolute scale corresponding to the electrochemical potentials measured in a concrete CV experimental setting, if the calculated value is compared with the value measured for the same compound and the obtained difference is taken into account as a correction for the values calculated for other compounds.

Preferably, the semiconducting material comprising the benzo-naphtofurane structural moiety serves as an electron transporting material or as an electron injecting material.

Besides the electron transport matrix compound, the semiconducting material according to the invention may comprise an electrical dopant. The electrical dopant may be either a redox dopant, or a metal salt or metal complex. Preferred n-dopants are metals in a substantially elemental form, or lithium salts and/or complexes comprising lithium cation. Preferably, the electron transport compound and the electrical dopant are comprised in the semiconducting material at least partly in form of a homogeneous mixture, wherein both components are molecularly dispersed in each other.

The objective of the invention is further achieved by an electronic device comprising at least one semiconducting material according to the invention, preferably in form of an electronic device wherein the inventive semiconducting material forms at least one layer between two electrodes. In a device operated under direct current, the electrode which is electrically connected with the negative pole of the source of electricity may be assigned as a cathode and the electrode electrically connected to the negative pole of the electricity source as an anode.

Specifically, the second object of the invention is represented by an electronic device comprising at least one semiconducting layer comprising the semiconducting material according to the invention or consisting of it. More specifically, the semiconducting material according to the invention is used in the electronic device in an electron transporting layer, in an electron injecting layer, or in a layer having double electron transporting and hole blocking function.

In specific cases, also exciton blocking function can be considered.

Another object of the invention is a compound comprising at least one structural moiety having formula (II)

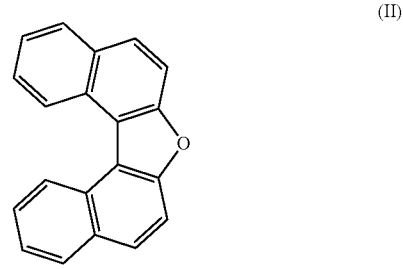 [SMILES: c1ccc2c(c1)ccc1oc3ccc4ccccc4c3c12]

(II)

and at least one polar structural moiety selected from
a) a structural moiety consisting of one atom of 15$^{th}$ group of the Periodic Table and one atom of 16$^{th}$ group of the Periodic Table linked together by a covalent bond, or
b) from a heteroaryl selected from pyridine-2-yl, pyridine-4-yl, quinoline-4-yl and 1,3,5-triazine-2-yl, or
c) from a benzimidazolyl moiety having formula (Ia) or (Ib)

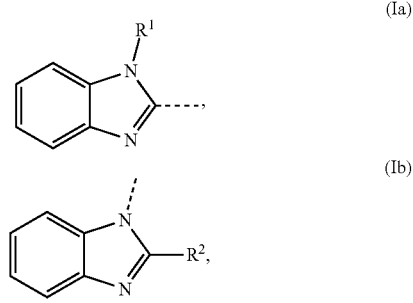

(Ia)

(Ib)

wherein the dashed line represents the bond attaching the benzimidazolyl moiety of formula (Ia) or (Ib) to other structural moieties of the molecule and R$^1$ and R$^2$ are selected from
(i) C$_1$-C$_{24}$ alkyl,
(ii) C$_3$-C$_{24}$ cycloalkyl,
(iii) C$_6$-C$_{24}$ aryl,
(iv) C$_7$-C$_{24}$ arylalkyl,
(v) C$_3$-C$_{24}$ heteroalkyl or C$_4$-C$_{24}$ heterocycloalkyl or C$_8$-C$_{24}$ aryl-heteroalkyl each comprising at least one heteroatom selected from Si and Ge,
(vi) C$_2$-C$_{24}$ heteroalkyl or C$_3$-C$_{24}$ heterocycloalkyl or C$_7$-C$_{24}$ aryl-heteroalkyl each comprising at least one heteroatom selected from B and P. and from
(vii) C$_2$-C$_{24}$ heteroaryl each comprising up to 4 heteroatoms independently selected from N, O and S.

The structural moiety having formula (II) and the polar structural moiety may be directly linked by a covalent bond or may be separated from each other by a linker structural moiety. In one of preferred embodiments, the linker structural moiety is a sterically rigid group. Typical examples of sterically rigid groups are polycyclic aliphatic or heteroaliphatic structural moieties, for example an adamantane or a norbornane structural moiety. Another example of sterically rigid moieties are aromatic or heteroaromatic moieties, which may be either monocyclic or polycyclic. A specific example of polycyclic aromatic or heteroaromatic structural moieties are condensed polycyclic aromatic or heteroaromatic structural moieties.

The linker moiety may further allow a conjugation of delocalized electrons between the structural moiety having formula (II) and the polar structural moiety. In one of preferred embodiments, the linker between the structural moiety having formula (II) and the polar structural moiety is an arylene or heteroarylene linker. Preferably, the arylene linker or the heteroarylene linker comprises up to three aromatic rings and/or up to 24 carbon atoms. A preferred example of the arylene linker is a phenylene. The arylene and heteroaryelene linkers are both sterically rigid and allowing the conjugation of delocalized electrons between the structural moiety having formula (II) and the polar structural moiety.

The phenylene may be selected from ortho-, meta- and para-phenylene. For sterical reasons, m- and p-phenylene linkers are preferred.

Also preferably, the polar structural moiety or the linker bearing the polar structural moiety is attached to the structural moiety having formula (II) in the position in the formula (II) which is next (closest) to the oxygen heteroatom of the formula (II).

A typical polar structural moiety consisting of one atom of $15^{th}$ group of the Periodic Table and one atom of $16^{th}$ group of the Periodic Table linked together by a covalent bond is the phosphine oxide group. Preferably, the structural moieties directly attached to the phosphine oxide group are arene or heteroarene structural moieties. Examples of arene structural moieties are aryl or arylene groups, examples of heteroarene structural moieties are heteroaryl or heteroarylene groups. In one embodiment of the invention, the polar structural moiety consists of one atom of $15^{th}$ group of the Periodic Table and one atom of $16^{th}$ group of the Periodic Table linked together by a covalent bond and its atom of $15^{th}$ group of the Periodic Table is member of a covalent ring structure. An example of such polar structural moiety attached to covalent ring structure can be a phosphine oxide group substituted with at least two structural units selected from arylene and heteroarylene, wherein the at least two structural units are linked together to form a ring.

If not explicitly stated that a group or structural unit is unsubstituted, the structural unit may be substituted and the count of atoms (e.g., count of carbon atoms) given for it then comprises also possible substituents. The number of carbon atoms or heteroatoms comprised in the compound comprising the structural moiety having the formula (II) is not specifically limited. Should the compound comprising the structural moiety having the formula (II) be used in a VTE process, it is advantageous that its relative molecular weight is roughly in the range 200-1200, preferably in the range 300-1000), more preferably in the range 400-900, even more preferably in the range 500-800.

It is desirable that the size of the polar structural moiety, of the optional linker between the polar structural moiety and the structural moiety having formula (II), and the number and the size of the substituents tuning the properties of the compound comprising the structural moiety having the formula (II) are commensurate to the number of structural moieties having the formula (II). It is preferred that the structural moieties having formula (II) comprise not less than 20% of the overall count of carbon atoms in the electron transport matrix compound, more preferably not less than 30% of the overall count of carbon atoms, even more preferably not less than 40% and most preferably not less than 50% of the overall count of carbon atoms in the compound comprising the structural moiety having the formula (II).

Preferred substituents are structural moieties which are thermally and chemically stable. The term "chemical stability" is used in the sense that stable groups do not exhibit, under conditions of use in the semiconducting material, a detectable reactivity with auxiliary compounds (for example with typical electrical dopants that serve for improving electrical properties of doped semiconducting materials) or with ambient conditions (e.g. a reactivity with moisture or a light-induced reactivity). Substituents may serve for tuning the processability or electronic properties of the compound comprising the structural moiety having the formula (II).

Examples of stable electron donating substituents are alkyl, alkylene, heteroalkyl or heteroalkylene structural moieties, like methyl group, methoxy group, ethyl group, ethoxy group, methylenedioxy group, alkylthio group, and five-membered heterocyclic structural moieties comprising up to three heteroatoms selected from N, O and S. Examples of sufficiently stable electron withdrawing structural moieties are halogen atoms, halogenated or perhalogenated alkyl groups, six-membered nitrogen-containing heteroaryl or heteroarylene moieties like pyridyl, diazinyl, triazinyl, bis (pyridine)-diyl, phenanthrene-diyl, halogenated or perhalogenated aryl groups, halogenated or perhalogenated arylene groups, halogenated or perhalogenated heteroaryl groups, halogenated or perhalogenated heteroarylene groups, nitrile groups, nitro groups, electron withdrawing heteroaryls.

For example, it is well-known that electron withdrawing strength of a substituted or unsubstituted aryl, arylene, heteroaryl or heteroarylene structural moiety may be augmented by its substitution with nitrile groups, acyl groups, aryl groups, arylsulfonyl groups and other electron withdrawing groups, whereas the substitution with electron donating groups will decrease the electron withdrawing strength of the same structural moiety.

Every additional advantageous structural feature recited above for the use of electron transport matrix compound comprising the structural moiety having the formula (II) in the semiconducting material according to the invention makes advantageous also the compound comprising the structural moiety having the formula (II) itself.

III. BRIEF DESCRIPTION OF THE DRAWINGS

IV. DETAILED DESCRIPTION OF THE INVENTION

The semiconducting material according to the invention is particularly advantageous for use in OLEDs. Therefore, this embodiment of the inventive device will be further described in detail.

Device Architecture

Figure 1:
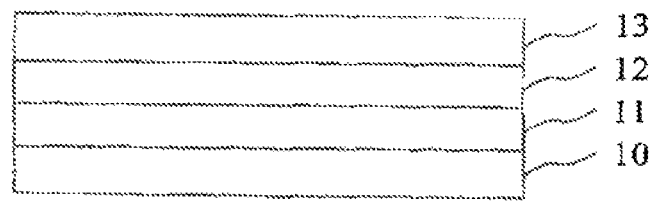
FIG. 1 shows a schematic illustration of a device in which the present invention can be incorporated.

FIG. 1 shows a stack of anode (10), organic semiconducting layer (11) comprising the light emitting layer (EML), electron transporting layer (ETL) (12), and cathode (13). Other layers can be inserted between those depicted, as explained herein.

Figure 2:
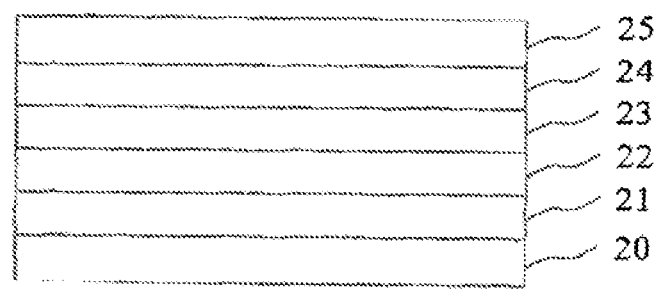
FIG. 2 shows a schematic illustration of a device in which the present invention can be incorporated.

FIG. 2 shows a stack of an anode (20), a hole injecting and transporting layer (21), a hole transporting layer (22) which can also aggregate the function of electron blocking, an EML (23), an ETL (24), and a cathode (25). Other layers can be inserted between those depicted, as explained herein.

The wording "device" comprises the organic light emitting diode.

Material Properties—Energy Levels

A method to determine the ionization potentials (IP) is the ultraviolet photoelectron spectroscopy (UPS). It is usual to measure the ionization potential for solid state materials; however, it is also possible to measure the IP in the gas phase. Both values are differentiated by their solid state effects, which are, for example the polarization energy of the holes that are created during the photo ionization process. A typical value for the polarization energy is approximately 1 eV, but larger discrepancies of the values can also occur. The IP is related to beginning of the photoemission spectra in the region of the large kinetic energy of the photoelectrons, i.e. the energy of the most weakly bounded electrons. A related method to UPS, the inverted photo electron spectroscopy (IPES) can be used to determine the electron affinity (EA). However, this method is less common. Electrochemical measurements in solution are an alternative to the determination of solid state oxidation ($E_{ox}$) and reduction ($E_{red}$) potential. An adequate method is for example the cyclovoltammetry (CV). A simple rule is used very often for the conversion of red/ox potentials into electron affinities and ionization potential: IP=4.8 eV+e*$E_{ox}$ (vs. ferrocenium/ferrocene ($Fc^+/Fc$)) and EA=4.8 eV+e*$E_{red}$ (vs. $Fc^+/Fc$) respectively (see B. W. D'Andrade, Org. Electron. 6, 11-20 (2005)). Processes are known for the correction of the electrochemical potentials in the case other reference electrodes or other redox pairs are used (see A. J. Bard, L. R. Faulkner, "Electrochemical Methods: Fundamentals and Applications", Wiley, 2. Ausgabe 2000)). The information about the influence of the solution used can be found in N. G. Connelly et al., Chem. Rev. 96, 877 (1996). It is usual, even if not exactly correct to use the terms "energy of the HOMO" $E_{(HOMO)}$ and "energy of the LUMO" $E_{(LUMO)}$ respectively as synonyms for the ionization energy and electron affinity (Koopmans theorem). It has to be taken in consideration, that the ionization potentials and the electron affinities are given in such a way that a larger value represents a stronger binding of a released or respectively of an absorbed electron. The energy scale of the frontier molecular orbitals (HOMO, LUMO) is opposed to this. Therefore, in a rough approximation, is valid: IP=$-E_{(HOMO)}$ and EA=$E_{(LUMO)}$. The given potentials correspond to the solid-state potentials.

Substrate

It can be flexible or rigid, transparent, opaque, reflective, or translucent. The substrate should be transparent or translucent if the light generated by the OLED is to be transmitted through the substrate (bottom emitting). The substrate may be opaque if the light generated by the OLED is to be emitted in the direction opposite of the substrate, the so called top-emitting type. The OLED can also be transparent. The substrate can be either arranged adjacent to the cathode or anode.

Electrodes

The electrodes are the anode and the cathode, they must provide a certain amount of conductivity, being preferentially conductors. Preferentially the "first electrode" is the cathode. At least one of the electrodes must be semi-transparent or transparent to enable the light transmission to the outside of the device. Typical electrodes are layers or a stack of layer, comprising metal and/or transparent conductive oxide. Other possible electrodes are made of thin busbars (e.g. a thin metal grid) wherein the spaces between the busbars is filled (coated) with a transparent material with a certain conductivity, such as graphene, carbon nanotubes, doped organic semiconductors, etc.

In one mode, the anode is the electrode closest to the substrate, which is called non-inverted structure. In another mode, the cathode is the electrode closest to the substrate, which is called inverted structure.

Typical materials for the anode are ITO and Ag. Typical materials for the cathode are Mg:Ag (10 vol. % of Mg), Ag, ITO, Al. Mixtures and multilayer are also possible.

Preferably, the cathode comprises a metal selected from Ag, Al, Mg, Ba, Ca, Yb, In, Zn, Sn, Sm, Bi, Eu, Li, more preferably from Al, Mg, Ca, Ba and even more preferably selected from Al or Mg. Preferred is also a cathode comprising an alloy of Mg and Ag.

Hole-Transporting Layer (HTL)

It is a layer comprising a large gap semiconductor responsible to transport holes from the anode or holes from a CGL to the EML. The HTL is comprised between the anode and the EML or between the hole generating side of a CGL and the EML. The HTL can be mixed with another material, for example a p-dopant, in which case it is said the HTL is p-doped. The HTL can be comprised by several layers, which can have different compositions. P-doping the HTL lowers its resistivity and avoids the respective power loss due to the otherwise high resistivity of the undoped semiconductor. The doped HTL can also be used as optical spacer, because it can be made very thick, up to 1000 nm or more without significant increase in resistivity.

Suitable hole transport materials (HTM) can be, for instance HTM from the diamine class, where a conjugated system is provided at least between the two diamine nitrogens. Examples are N4,N4'-di(naphthalen-1-yl)-N4,N4'-diphenyl-[1,1'-biphenyl]-4,4'-diamine (HTM1), N4,N4, N4'', N4''-tetra([1,1'-biphenyl]-4-yl)-[1,1':4',1''-terphenyl]-4,4''-diamine (HTM2) or N4,N4''-di(naphthalen-1-yl)-N4,N4''-diphenyl-[1,1':4',1''-terphenyl]-4,4''-diamine (HTM3). The synthesis of diamines is well described in literature; many diamine HTMs are readily commercially available.

Hole-Injecting Layer (HIL)

Is a layer which facilitates the injection of holes from the anode or from the hole generating side of a CGL into an adjacent HTL. Typically the HIL is a very thin layer (<10 nm). The hole injection layer can be a pure layer of p-dopant and can be about 1 nm thick. When the HTL is doped, an HIL may not be necessary, since the injection function is already provided by the HTL.

Light-Emitting Layer (EML)

The light emitting layer must comprise at least one emission material and can optionally comprise additional layers. If the EML comprises a mixture of two or more materials the charge carrier injection can occur in different materials for instance in a material which is not the emitter, or the charge carrier injection can also occur directly into the emitter. Many different energy transfer processes can occur inside the EML or adjacent EMLs leading to different types of emission. For instance excitons can be formed in a host material and then be transferred as singlet or triplet excitons to an emitter material which can be singlet or triplet emitter which then emits light. A mixture of different types of emitter can be provided for higher efficiency. Mixed light can be realized by using emission from an emitter host and an emitter dopant.

Blocking layers can be used to improve the confinement of charge carriers in the EML, these blocking layers are further explained in U.S. Pat. No. 7,074,500 B2.

Electron-Transporting Layer (ETL)

Is a layer comprising a large gap semiconductor responsible to transport electrons from the cathode or electrons from a CGL or EIL (see below) to the EML. The ETL is comprised between the cathode and the EML or between the electron generating side of a CGL and the EML. The ETL can be mixed with an electrical n-dopant, in which case it is said the ETL is n-doped. The ETL can comprise several layers, which can have different compositions. Electrical n-doping the ETL lowers its resistivity and/or improves its ability to inject electrons into an adjacent layer and avoids the respective power loss due to the otherwise high resistivity (and/or bad injection ability) of the undoped semiconductor. The doped ETL can also be used as optical spacer, because it can be made very thick, up to 1000 nm or more without significant increase in resistivity.

Other layers with different functions can be included, and the device architecture can be adapted as known by the skilled in the art. For example, an electron-injecting layer (EIL) can be used between the cathode and the ETL. Also the EIL can comprise the inventive matrix compounds of the present application.

Charge Generation Layer (CGL)

The OLED can comprise a CGL which can be used in conjunction with an electrode as inversion contact, or as connecting unit in stacked OLEDs. A CGL can have the most different configurations and names, examples are pn-junction, connecting unit, tunnel junction, etc. Examples of pn junctions are disclosed in US 2009/0045728 A1, US 2010/0288362 A1. Metal layers and or insulating layers can also be used.

Stacked OLEDs

When the OLED comprises two or more EMLs separated by CGLs, the OLED is called a stacked OLED, otherwise it is named a single unit OLED. The group of layers between two closest CGLs or between one of the electrodes and the closest CGL is named a electroluminescent unit (ELU). Therefore a stacked OLED can be described as anode/$ELU_1$/ $\{CGL_X/ELU_{1+X}\}_X$/cathode, wherein x is a positive integer and each $CGL_X$ or each $ELU_{1+x}$ can be equal or different. The CGL can also be formed by the adjacent layers of two ELUs as disclosed in US2009/0009072 A1. Further stacked OLEDs are explained e.g. in US 2009/0045728 A1, US 2010/0288362 A1, and references therein.

Deposition of Organic Layers

Any organic semiconducting layers of the inventive display can be deposited by known techniques, such as vacuum thermal evaporation (VTE), organic vapour phase deposition, laser induced thermal transfer, spin coating, blade coating, slot dye coating, inkjet printing, etc. A preferred method for preparing the OLED according to the invention is VTE.

Preferably, the ETL is formed by evaporation. When using an additional material in the ETL, it is preferred that the ETL is formed by co-evaporation of the electron transporting matrix (ETM) and the additional material. The additional material may be mixed homogeneously in the ETL. In one mode of the invention, the additional material has a concentration variation in the ETL, wherein the concentration changes in the direction of the thickness of the stack of layers. It is also foreseen that the ETL is structured in sub-layers, wherein some but not all of these sub-layers comprise the additional material.

Electrical Doping

The present invention can be used in addition or in combination with electrical doping of organic semiconducting layers.

The most reliable and at the same time efficient OLEDs are OLEDs comprising electrically doped layers. Generally, the electrical doping means improving of electrical properties, especially the conductivity and/or injection ability of a doped layer in comparison with neat charge-transporting matrix without a dopant. In the narrower sense, which is usually called redox doping or charge transfer doping, hole transport layers are doped with a suitable acceptor material (p-doping) or electron transport layers with a donor material (n-doping), respectively. Through redox doping, the density of charge carriers in organic solids (and therefore the conductivity) can be increased substantially. In other words, the redox doping increases the density of charge carriers of a semiconducting matrix in comparison with the charge carrier density of the undoped matrix. The use of doped charge-carrier transport layers (p-doping of the hole transport layer by admixture of acceptor-like molecules, n-doping of the electron transport layer by admixture of donor-like molecules) in organic light-emitting diodes is, e.g., described in US 2008/203406 and U.S. Pat. No. 5,093,698.

US2008227979 discloses in detail the charge-transfer doping of organic transport materials, with inorganic and with organic dopants. Basically, an effective electron transfer occurs from the dopant to the matrix increasing the Fermi level of the matrix. For an efficient transfer in a p-doping case, the LUMO energy level of the dopant is preferably more negative than the HOMO energy level of the matrix or at least slightly more positive, not more than 0.5 eV, to the HOMO energy level of the matrix. For the n-doping case, the HOMO energy level of the dopant is preferably more positive than the LUMO energy level of the matrix or at least slightly more negative, not lower than 0.5 eV, to the LUMO energy level of the matrix. It is further more desired that the energy level difference for energy transfer from dopant to matrix is smaller than + 0.3 eV.

Typical examples of known redox doped hole transport materials are: copper phthalocyanine (CuPc), which HOMO level is approximately −5.2 eV, doped with tetrafluoro-tetracyanoquinonedimethane (F4TCNQ), which LUMO level is about −5.2 eV; zinc phthalocyanine (ZnPc) (HOMO: −5.2 eV) doped with F4TCNQ; a-NPD (N,N'-Bis(naphthalen-1-yl)-N,N'-bis(phenyl)-benzidine) doped with F4TCNQ. a-NPD doped with 2,2'-(perfluoronaphthalene-2,6-diylidene) dimalononitrile (PD1). a-NPD doped with 2,2', 2"-(cyclopropane-1,2,3-triylidene)tris(2-(p-cyanotetrafluorophenyl)acetonitrile) (PD2). All p-doping in the device examples of the present application was done with 8 wt. % PD2.

Typical examples of known redox doped electron transport materials are: fullerene C60 doped with acridine orange base (AOB); perylene-3,4,9,10-tetracarboxylic-3,4,9,10-dianhydride (PTCDA) doped with leuco crystal violet; 2,9-di(phenanthren-9-yl)-4,7-diphenyl-1,10-phenanthroline doped with tetrakis (1,3,4,6,7,8-hexahydro-2H-pyrimido[1, 2-a] pyrimidinato) ditungsten(II) ($W_2(hpp)_4$); naphthalene tetracarboxylic acid di-anhydride (NTCDA) doped with 3,6-bis-(dimethyl amino)-acridine; NTCDA doped with bis (ethylene-dithio) tetrathiafulvalene (BEDT-TTF).

In the present invention, classical redox dopants with high reduction strength, expressed as a highly negative redox potential measured by cyclic voltammetry (CV) in THF vs. Fc+/Fc standard, can be successfully replaced with metal salts having no pronounced reductive properties. True mechanism how these compounds, sometimes called "electrically doping additives", contribute to the lowering of the voltage in electronic devices, is not yet known.

Typical known representative of such metal salts is lithium 8-hydroxyquinolinolate (LiQ) represented by the formula D1

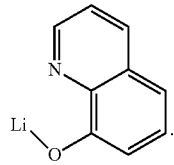

D1

Many other similar lithium complexes comprising five- or six-membered chelate ring wherein Li is coordinated to an oxygen and a nitrogen atom are known and were used or proposed as electrical dopants for organic electron transporting semiconducting materials.

It was found that in the doped semiconducting material according to present invention, better performance in comparison with D1 is achieved with lithium salt having general formula (III)

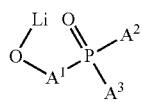

Formula (III)

wherein $A^1$ is a $C_6$-$C_{30}$ arylene or $C_2$-$C_{30}$ heteroarylene comprising at least one atom selected from O, S and N in an aromatic ring and each of $A^2$-$A^3$ is independently selected from a $C_6$-$C_{30}$ aryl and $C_2$-$C_{30}$ heteroaryl comprising at least one atom selected from O, S and N in an aromatic ring, wherein any aryl, arylene, heteroaryl and/or heteroarylene may be independently unsubstituted or substituted with groups selected from hydrocarbon groups comprising only C and H, alkoxy, aryloxy and lithiumoxy, provided that the given C count in an aryl, heteroaryl, arylene or heteroarylene group includes also all substituents present on the said group.

It is to be understood that the term substituted or unsubstituted arylene stands for a divalent radical derived from substituted or unsubstituted arene, wherein the both adjacent structural moieties (in formula (III), the OLi group and the diaryl prosphine oxide group) are attached directly to an aromatic ring of the arylene group. Similarly, the term substituted or unsubstituted heteroarylene stands for a divalent radical derived from substituted or unsubstituted heteroarene, wherein the both adjacent structural moieties (in formula (III), the OLi group and the diaryl prosphine oxide group) are attached directly to an aromatic ring of the heteroarylene group. In examples of the present application, this class of dopants is represented by compounds D2 and D3

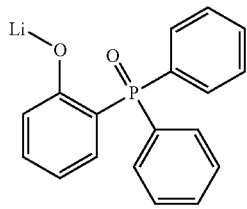

D2

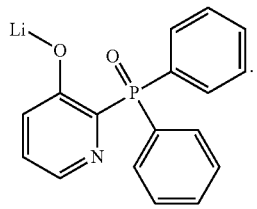

D3

Compound D2 was disclosed in the application PCT/EP2012/074127, published as WO2013/079678 A1, and compound D3 in the application EP 2 811 000.

Preferred ETL matrix compounds of the present invention are

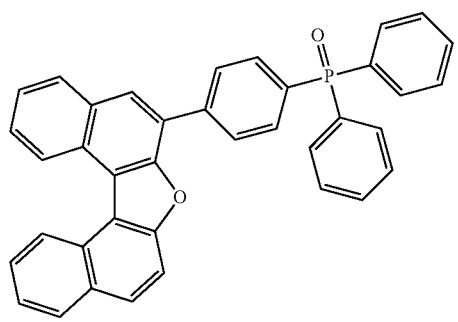

A1

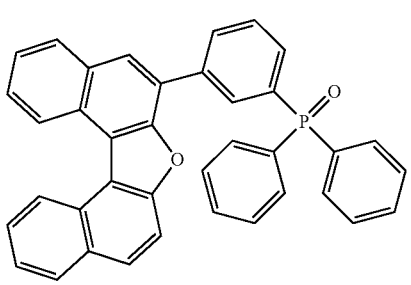

A2

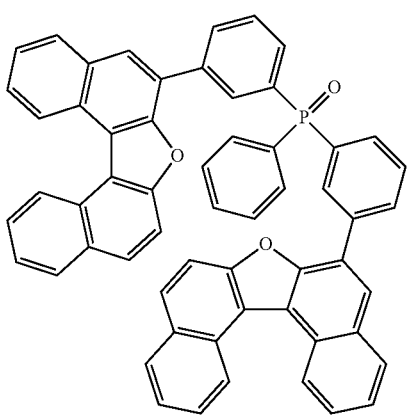

A3

-continued

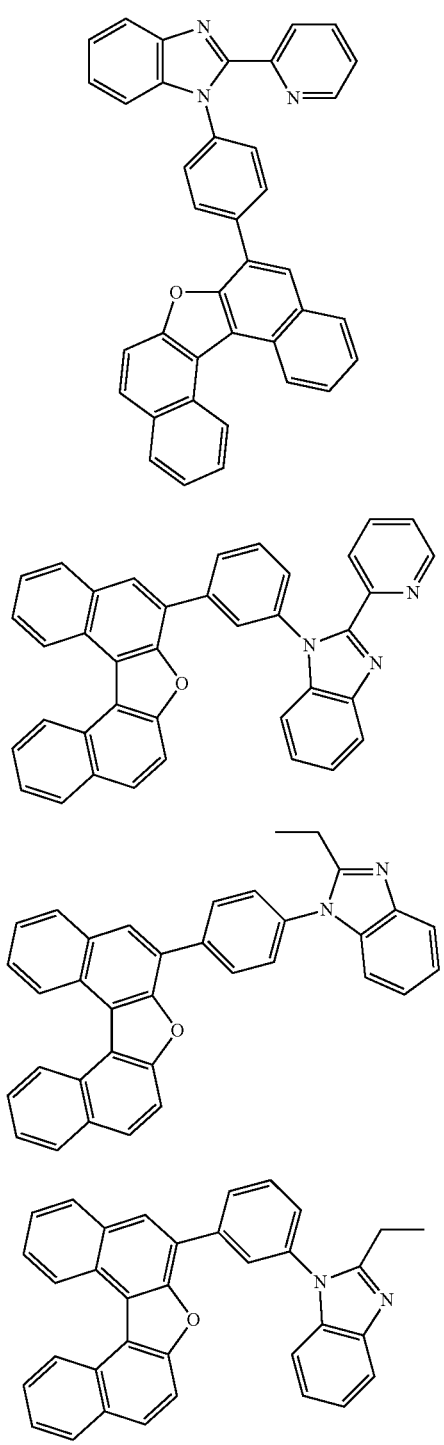

A4

A5

A6

A7 naphtofurane electron transporting structural moiety. Following comparative compounds are referred to:

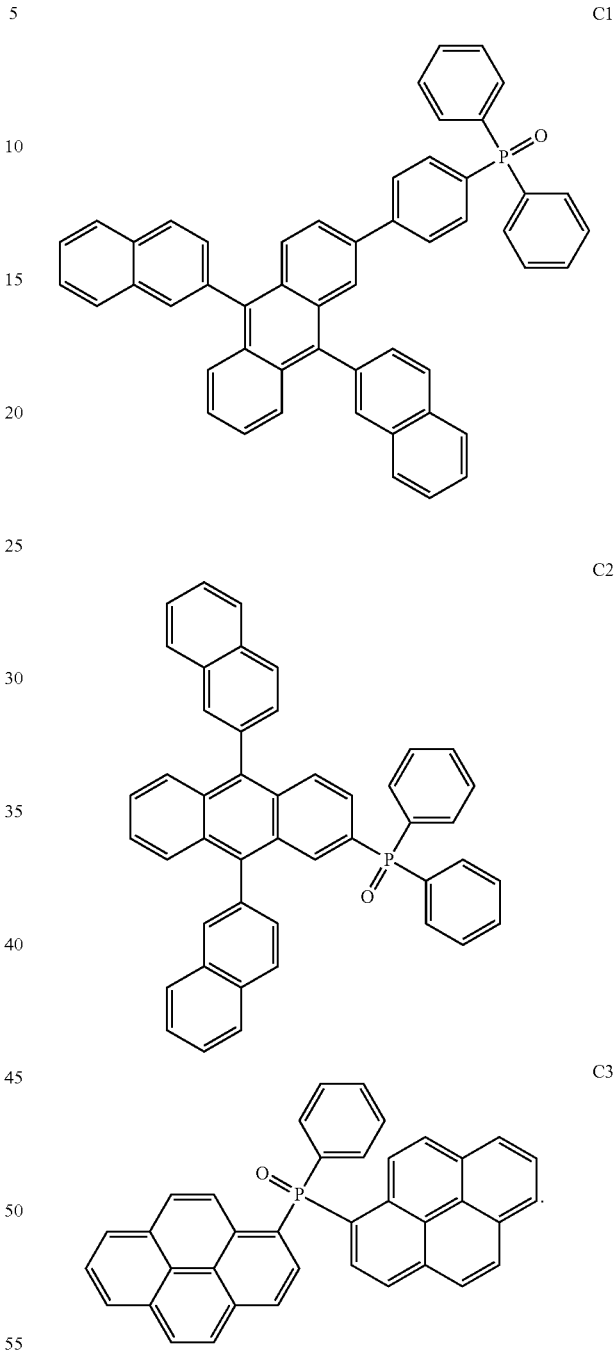

C1

C2

C3

V. ADVANTAGEOUS EFFECT OF THE INVENTION

The favourable effects of the inventive semiconducting materials are shown in comparison with comparative devices comprising instead of the inventive compounds electron transporting matrices which lack the inventive combination of the polar structural moiety and the benzo- Table 1 shows the performance of inventive and comparative compounds in bottom emission structured OLEDs, described in detail in example 1, with respect to voltage (U) and quantum efficiency (Qeff). Additionally the quotient Qeff/U (power efficiency) is taken as basis for enabling proper comparison in order to consider tradeoff effects between both values. The LUMO energies are represented by reversible electrochemical redox potentials of the studied compounds, measured by CV in THF against $Fc^+/Fc$ reference redox system.

TABLE 1

| Code | LUMO (V) | D1 doped | | | D2 doped | | | Mg doped | | |
|------|----------|----------|------|------|----------|------|------|----------|------|------|
|      |          | U (V)    | Qeff | Q/U  | U (V)    | Qeff | Q/U  | U (V)    | Qeff | Q/U  |
| A1   | −2.47    | 5.1      | 5.6  | 1.10 | 4.8      | 7.1  | 1.48 | 3.7      | 5.6  | 1.51 |
| A2   | −2.44    | 4.0      | 6.0  | 1.50 | 3.9      | 6.3  | 1.62 |          |      |      |
| A3   |          | 4.8      | 5.7  | 1.19 | 4.5      | 7.2  | 1.6  |          |      |      |
| C1   | −2.27    | 4.3      | 5.0  | 1.16 | 4.3      | 5.9  | 1.37 |          |      |      |
| C2   | −2.19    | 4.6      | 5.2  | 1.13 | 5.0      | 4.4  | 0.88 | 4.2      | 1.0  | 0.24 |
| C3   | −2.24    | 4.2      | 5.1  | 1.21 | 4.1      | 5.8  | 1.41 |          |      |      |

EXAMPLES

General Remarks for Synthesis:

All reactions were carried out under argon atmosphere using oven dried glassware. Starting materials were used as purchased without further purification. Materials, which were used to build OLEDs, were sublimed by gradient sublimation to achieve highest purity. Following general procedures, well-known in the art, are applicable for the synthesis of electron transport matrix compounds comprising benzo-naphtofurane structural moiety and a polar structural moiety according to invention.

General Procedure A: Triphenylphosphinoxide Synthesis

The halogen compound was dissolved in THF. 2.5M n-BuLi solution in hexane was slowly dropped to this solution chilled to −80° C. (temperature measured directly in the solution). The stirring was continued for one hour. Diphenyl phosphine chloride or phenylphosphine dichloride, respectively, was added slowly at −80° C. The reaction mixture was allowed to warm to room temperature (RT) and stirred overnight. After methanol addition and reduction to dryness, the residue was dissolved in dichloromethane (DCM). The organic phase was washed with water, dried over $Na_2SO_4$ and reduced to dryness.

The residue was dissolved in DCM again and oxidized with 30 wt. % aqueous hydrogen peroxide solution. After stirring overnight, the organic solution was washed with water, dried over $Na_2SO_4$ and reduced to dryness. The crude product was purified by column chromatography.

General Procedure B: Suzuki Coupling

The halogen compound, the boronic acid, $Pd(P^tBu_3)_4$ and the solvent were mixed together. A degassed 2M aqueous $K_2CO_3$ solution was added. The mixture was stirred at 85° C. (oil bath temperature) for 18 h and cooled afterwards. In case that a solid precipitated, the solid was filtered off and purified by column chromatography directly. Otherwise, the organic phase was washed with water, dried over $Na_2SO_4$, reduced to dryness and purified by column chromatography afterwards.

(4-bromophenyl)diphenylphosphine Oxide

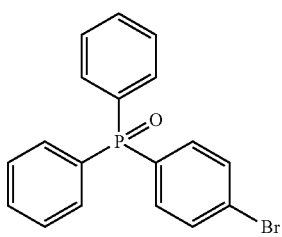 [SMILES: O=P(c1ccccc1)(c1ccccc1)c1ccc(Br)cc1]

According to general procedure A)
1,4-dibromobenzene: 10.00 g (42.4 mmol, 1.0 eq)
n-butyllithium, 2.5M in hexane: 17 mL (42.4 mmol, 1.0 eq)
chlorodiphenylphosphine: 9.35 g (42.4 mmol, 1.0 eq)
THF: 50 mL
DCM: 50 mL
$H_2O_2$, 30 wt. % in water: 10 mL.
Column chromatography: $SiO_2$, ethyl acetate
Yield: 6.84 g white solid (45% theoretical)
mp: 166° C.
GC-MS: m/z=356, 358

Bis(4-bromophenyl)(phenyl)phosphine Oxide

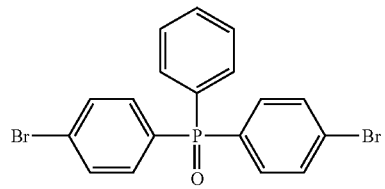 [SMILES: O=P(c1ccccc1)(c1ccc(Br)cc1)c1ccc(Br)cc1]

According to general procedure A
1,4-dibromobenzene: 10.00 g (42.4 mmol, 1.0 eq)
n-butyl lithium, 2.5M in hexane: 17 mL (42.4 mmol, 1.0 eq)
dichlorophenylphosphine: 3.79 g (21.2 mmol, 0.5 eq), dissolved in 50 mL THF
THF: 100 mL
DCM: 50 mL
$H_2O_2$, 30 wt. % in water 10 mL
Column chromatography: $SiO_2$, ethyl acetate
Yield: 5.0 g viscous oil (54%)
mp: 125° C.
GC-MS: m/z=433, 435, 437

(3-bromophenyl)diphenylphosphine Oxide

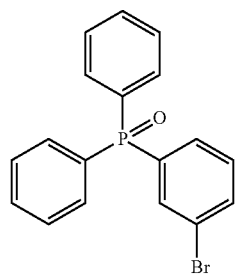 [SMILES: O=P(c1ccccc1)(c1ccccc1)c1cccc(Br)c1]

According to general procedure A
1,3-dibromobenzene: 10.00 g (42.4 mmol, 1.0 eq)
n-butyl lithium, 2.5M in hexane: 17 mL (42.4 mmol, 1.0 eq)
chlorodiphenylphosphine: 9.35 g (42.4 mmol, 1.0 eq)
THF: 50 mL
DCM: 50 mL
$H_2O_2$, 30 wt. % in water 10 mL
Column chromatography: $SiO_2$, ethyl acetate, $R_f$=0.52
Yield: 9.6 g white solid (63%)
mp: 95° C.
GC-MS: m/z=356, 358

Bis(3-bromophenyl)(phenyl)phosphine Oxide

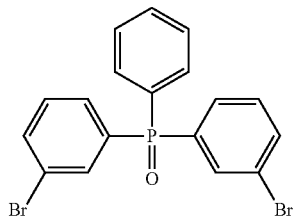 [SMILES: O=P(c1ccccc1)(c1cccc(Br)c1)c1cccc(Br)c1]

According to general procedure A 1,3-dibromobenzene: 10.00 g (42.4 mmol, 1.0 eq)
n-butyllithium, 2.5M in hexane: 17 mL (42.4 mmol, 1.0 eq)
dichlorophenylphosphine: 3.58 g (21.2 mmol, 0.5 eq), dissolved in 50 mL THF
THF: 100 mL
DCM: 50 mL
$H_2O_2$, 30 wt. % in water: 10 mL
Column chromatography: $SiO_2$, ethyl acetate
Yield: 6.86 g (74%) white solid
mp: 103° C.
GC-MS: m/z=434, 436, 438

1-(4-bromophenyl)-2-(pyridin-2-yl)-1H-benzo[d]imidazole

An oven-dried, two-necked, 1-L, round-bottomed flask equipped with a magnetic stirring bar, a septum and a reflux condenser, fitted with argon inlet, is charged with a 2-(pyridin-2-yl)-1H-benzo[d]imidazole (0.128 mmol, 1 eq.), 1-iodo-4-bromobenzene (19.2 mmol. 1.5 eq), copper iodide (0.042 mmol, 0.33 eq), 1,10-phenanthroline (0.081 mmol, 0.63 eq) and $Cs_2CO_3$ (0.1885 mmol, 1.45 eq). The flask is sealed, evacuated and back filled with argon. Anhydrous DMF (500 mL) is cannulated directly into reaction flask, septum is replaced by stopper, and the mixture is stirred under argon at 150° C. overnight. Reaction mixture is cooled down to RT, filtered through short Florisil pad (~3 cm) and evaporated to dryness. Residue is dissolved in chloroform, washed with an aqueous EDTA solution (1 wt. %), water (3×) and brine (1×), dried over magnesium sulfate, filtered and evaporated to dryness. Residue is triturated with iso-propyl alcohol overnight, filtered and dried. Finally, the solid is re-dissolved in dichloromethane, treated with 5 g $SiO_2$, filtered and evaporated to dryness.

1-(3-bromophenyl)-2-(pyridin-2-yl)-1H-benzo[d]imidazole

Was prepared analogously using 1-iodo-3-bromobenzene instead of 1-iodo-4-bromobenzene.

(4-(9,10-di(naphthalen-2-yl)anthracen-2-yl)phenyl)diphenylphosphine Oxide (C1)

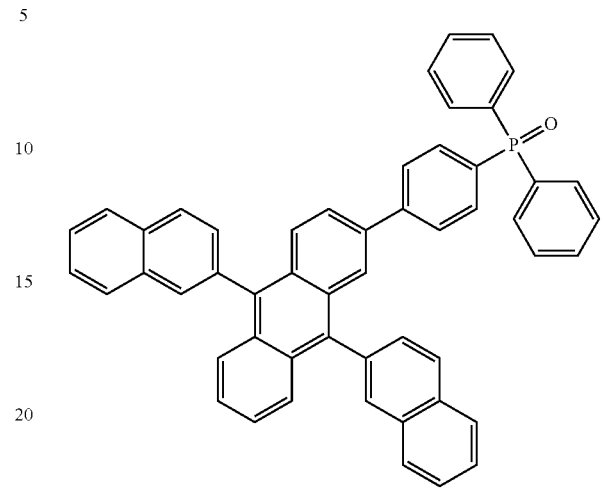

According to general procedure B Known from WO2012/173370 (LG, paragraph 131)

(4-bromophenyl)diphenylphosphine oxide: 1.88 g (5.3 mmol, 1.0 eq)
(9,10-di(naphthalen-2-yl)anthracen-2-yl)boronic acid: 3.0 g (6.3 mmol, 1.2 eq)
$Pd(PPh_3)_4$: 183 mg (0.16 mmol, 3 mol. %)
$K_2CO_3$, 2M: 8 mL
DME: 20 mL
Column chromatography: $SiO_2$, ethyl acetate
Yield: 3.0 g (81%) yellow solid
mp: n.a. (glassy)
EI-MS: nm/z=706

(9,10-di(naphthalen-2-yl)anthracen-2-yl)diphenylphosphine Oxide (C2)

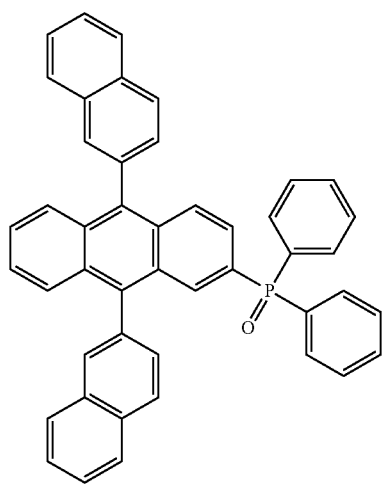 [SMILES: O=P(c1ccccc1)(c1ccccc1)c1ccc2c(-c3ccc4ccccc4c3)c3ccccc3c(-c3ccc4ccccc4c3)c2c1]

21

Synthesis According to General Procedure A)

2-bromo-9,10-di(naphth-2-yl)-anthracene: 5.00 g (1.0 eq, 9.81 mmol)
n-butyl lithium, 2.5M in hexane: 4.7 mL (1.2 eq, 11.77 mmol)
THF: 50 mL
chlorodiphenylphosphine: 2.1 mL (1.2 eq, 11.77 mmol)
DCM: 60 mL
$H_2O_2$, 30 wt. % in water: 15 mL
column chromatography ($SiO_2$, hexane:EE 1:1)
Yield: 3.20 g (52%)
Melting point: none (glassy compound)
ESI-MS: m/z=631 (M+H$^+$)

Phenyldi(pyren-1-yl)phosphine Oxide (C3)

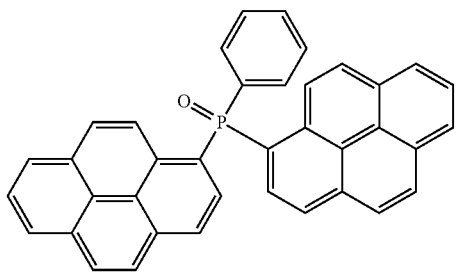 [SMILES: O=P(c1ccccc1)(c1ccc2ccc3cccc4ccc1c2c34)c1ccc2ccc3cccc4ccc1c2c34]

Known for long (CAS721969-93-3), commercially available, e.g. from Luminescence Technology Corp (TW).
Dopants:

Lithium Quinolin-8-olate (D1)

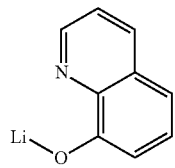

Commercially available

22

Lithium 2-(diphenylphosphoryl)phenolate (D2)

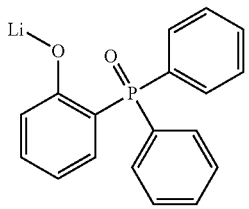

Synthesis According to Patent Application WO2013/079678 (Compound (1), p. 15-16)

Lithium 2-(diphenylphosphoryl)pyridin-3-olate (D3)

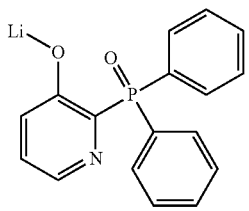

Synthesis According to Patent Application EP 2 811 000

Inventive Compounds

Bis(3-(dinaphtho[2,1-b:1',2'-d]furan-6-yl)phenyl)(phenyl)phosphine Oxide (A3)

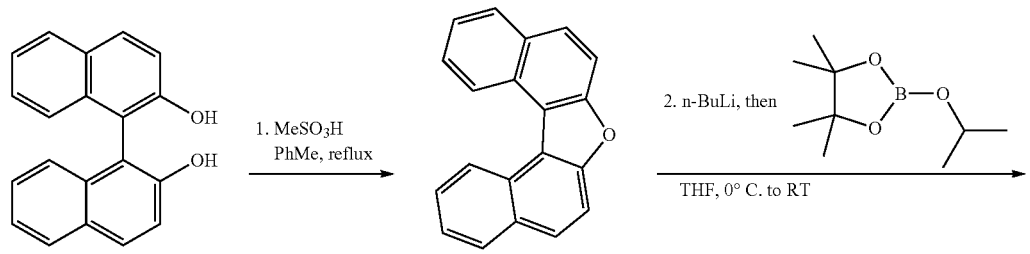

Chemical Formula: $C_{23}H_{14}O_2$
Molecular Weight: 266.33

Chemical Formula: $C_{20}H_{12}O$
Molecular Weight: 265.32

-continued

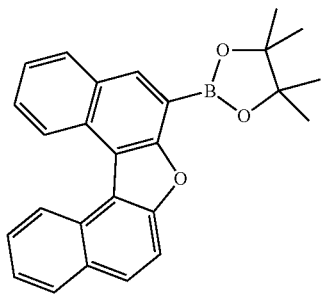

Chemical Formula: C₂₆H₂₃BO₃
Molecular Weight: 394.28

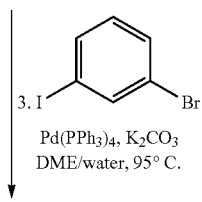

3.

Pd(PPh₃)₄, K₂CO₃
DME/water, 95° C.

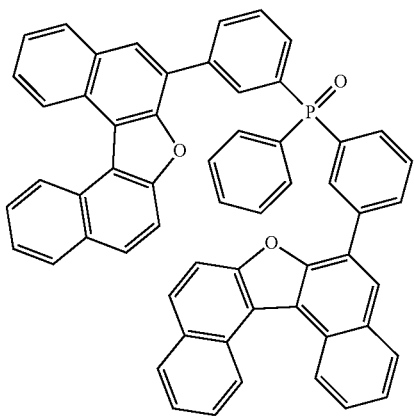

Chemical Formula: C₅₈H₃₅O₃P
Molecular Weight: 810.89

4.

HexLi, THF

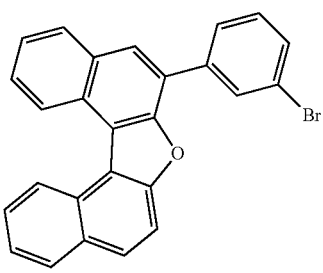

Chemical Formula: C₂₆H₁₅BrO
Molecular Weight: 423.31

Step 1: Dinaphtho[2,1-b:1',2'-d]furan

[1,1'-binaphthalene]-2,2'-diol (30.0 g, 0.105 mol, 1.0 eq.) was placed in a flask and flushed with argon. Anhydrous toluene (300 mL) was added, followed by trifluoromethanesulfonic acid (11.7 mL, 0.210 mol, 2.0 eq.). After further degassing, the mixture was refluxed under argon for 48 hours. After cooling, the reaction mixture was extracted with water (500 mL), dried over MgSO₄, and its volume has been reduced under vacuum until precipitation of a solid started. Hexane (300 mL) was then added, the resulting suspension was stirred for 2 h and the precipitate was filtered off. This solid was dissolved in dichloromethane (DCM) and flash-chromatographed over silica bed, with elution with hexane-DCM mixture having volume ratio 2:1. The volume of the main fraction was reduced to ca. 50 mL, the resulting crystals were filtered off and dried under vacuum at room temperature. Yield 19.9 g (71%).

Step 2: 2-(dinaphtho[2,1-b: 1',2'-d]furan-6-yl)-4,4,5,5-tetramethyl-1,3,2-dioxaborolane Dinaphtho[2,1-b:1',2'-d]furan (14.1 g, 52.6 mmol, 1.0 eq.) from the previous step was placed in a flask, degassed with argon, and dissolved in 100 mL anhydrous THF. The resulting solution was cooled down to 0° C., and n-butyllithium (36.2 mL, 57.8 mmol, 1.1 eq.) was added dropwise over a 20-min period. The resulting yellow suspension was stirred overnight at room temperature (RT), and then quenched by dropwise addition of 2-isopropoxy-4,4,5,5-tetramethyl-1,3,2-dioxaborolane (21.5 mL, 105.2 mmol, 2.0 eq.). After stirring for another 20 h, the mixture was evaporated to dryness to give an orange oil. The crude material was purified by chromatography over silica (elution with hexane-DCM 9:1 (v/v), then with DCM). Yield 14.5 g (70%).

Step 3: Synthesis of 6-(3-bromophenyl)dinaphtho[2,1-b: 1',2'-d]furan 2-(dinaphtho[2,1-b:1',2'-d]furan-6-yl)-4,4,5,5-tetramethyl-1,3,2-dioxaborolane (4.2 g, 10.7 mmol, 1.0 eq.). 1-bromo-3-iodobenzene (3.62 g, 12.8 mmol, 1.2 eq.), the Pd-catalyst (246 mg, 2 mol %), and the base (4.4 g, 32 mmol, 3.0 eq.) were placed in a flask and dissolved in 2.5:1 mixture of DME and water (56 mL). The resulting solution was deaerated with argon, refluxed for 2 h at 100° C. stirred at room temperature overnight and refluxed for additional 9 h at 100° C. the next day before cooling down to room temperature overnight. The formed precipitate was filtered off and washed with small amounts of water and DME. The product was recrystallized from 80 mL CHCl₃. The yellow solid collected by filtration was washed with small amounts of CHCl₃ and dried under vacuum to give a first crop of the product (2.34 g, 52%). The mother liquor was reduced to 20 mL. After cooling to room temperature overnight under stirring, the formed precipitate was filtered and washed with CHCl₃ to give a second crop (0.73 g, 16%).

Step 4: Synthesis of bis(3-(dinaphtho[2,1-b:1',2'-d]furan-6-yl)phenyl)(phenyl)phosphine Oxide 6-(3-bromophenyl)dinaphtho[2,1-b:1',2'-d]furan (3.0 g, 7.1 mmol, 1.0 eq) was placed in a flask under inert atmosphere and dissolved in THF (30 mL). The resulting suspension was cooled to ~80° C. before adding n-hexyllithium (as a 33% (w/w) solution in n-hexane, 7.1 mmol, 1.0 eq.) over 15 min. After stirring for 3 h at −80° C., dichloro(phenyl)phosphine (0.63 g, 3.5 mmol, 0.5 eq) dissolved in 20 mL anhydrous THF was added. After stirring at −80° C. for 1 h, the reaction mixture was allowed to warm up to room temperature. 3 mL MeOH were added to quench the reaction and the volume of the solution was reduced under reduced pressure. The resulting oil was dissolved in 200 mL CHCl₃ and the organic phase was washed with 2×150 mL water, dried over MgSO₄ and filtered. H₂O₂ (3.5 mL, 30% w/w aqueous solution) was added to the filtrate and the resulting mixture was stirred at RT overnight. It was washed with water (2×150 mL), the organic layer was dried over MgSO₄, and evaporated to dryness. The crude product (ca. 3.2 g) was then purified by two successive column chromatography steps: 1) silica, elution with DCM/MeOH 99:1, and 2) silica, elution with ethyl acetate. Finally, the solid was dissolved in CHCl₃ and precipitated with hexane. Yield 1.5 g. ESI-MS: m/z=1, found: 811.24 (M+H$^+$) theor: 811.23. Melting point: not observed.

Compounds A1 (mp 262° C., redox potential in THF against Fc$^+$/Fc reference −2.47 V) and A2 (mp 265° C., redox potential in THF against Fc$^+$/Fc reference −2.44 V) were prepared analogously.

1-(4-(dinaphtho[2,1-b:1',2'-d]furan-6-yl)phenyl)-2-(pyridin-2-yl)-1H-benzo[d]imidazole (A4; EP15162788, p. 94)

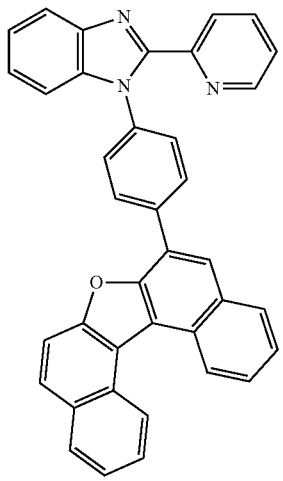 [SMILES: c1ccc(-c2nc3ccccc3n2-c2ccc(-c3cc4ccccc4c4c3oc3ccc5ccccc5c34)cc2)nc1]

Obtained using general Suzuki coupling procedure from 2-(dinaphtho[2,1-b: 1',2'-d]furan-6-yl)-4,4,5,5-tetramethyl-1,3,2-dioxaborolane and 1-(4-bromophenyl)-2-(pyridin-2-yl)-1H-benzo[d]imidazole.

mp 271° C., redox potential in THF against Fc$^+$/Fc reference −2.54 V 1-(3-(dinaphtho[2,1-b:1',2'-d]furan-6-yl)phenyl)-2-(pyridin-2-yl)-1H-benzo[d]imidazole (A5; EP15162788, p. 95)

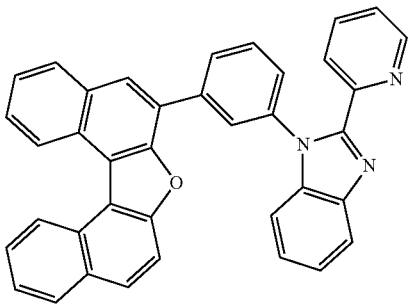 [SMILES: c1ccc(-c2nc3ccccc3n2-c2cccc(-c3cc4ccccc4c4c3oc3ccc5ccccc5c34)c2)nc1]

Obtained using general Suzuki coupling procedure from 2-(dinaphtho[2,1-b:1',2'-d]furan-6-yl)-4,4,5,5-tetramethyl-1,3,2-dioxaborolane and 1-(3-bromophenyl)-2-(pyridin-2-yl)-1H-benzo[d]imidazole.

Compounds A6 (mp 242° C., redox potential in THF against Fc$^+$/Fc reference −2.52 V) and A7 (mp 255° C.) were prepared analogously.

Analytics:

Final materials were characterized by mass spectrometry (MS) and proton magnetic resonance ($^1$H-NMR). NMR samples were dissolved in CD₂Cl₂ unless otherwise stated. Melting points (mp) were determined by differential scanning calorimetry (DSC). Peak temperatures are reported. If gas chromatography-mass spectrometry (GC-MS) or high performance liquid chromatography (HPLC) with electrospray ionization mass spectroscopy (ESI-MS) were used for the product characterization, only the mass/charge (m/z) ratios for the molecular peak are reported. For brominated intermediates, the corresponding isotopic multiplet is reported.

Auxiliary Procedures

Cyclic Voltammetry

The redox potentials given at particular compounds were measured in an argon deaerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode, consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard Fc$^+$/Fc redox couple, afforded finally the values reported above. All studied phosphine oxide compounds as well as the reported comparative compounds showed well-defined reversible electrochemical behaviour.

Device Examples

All data shown here are typical examples. The data in table 1 are medians over typically 16 identical diodes, which are described in the following examples.

Example 1

Bottom emission blue emitting OLED was made by depositing a 10 nm layer of N4,N4"-di(naphthalen-1-yl)-N4, N4"-diphenyl-[1,1':4',1"-terphenyl]-4,4"-diamine (HTM3) doped with 2,2',2"-(cyclopropane-1,2,3-triylidene)tris(2-(p-cyanotetrafluorophenyl)acetonitrile) (PD2, matrix to dopant weight ratio 92:8) onto a 90 nm thick ITO-glass substrate, followed by an 120 nm undoped layer of HTM3. Subsequently, a blue fluorescent emitting layer of ABH113 (Sun Fine Chemicals) doped with NUBD370 (Sun Fine Chemicals) (97:3 weight ratio) was deposited with a thickness of 20 nm. A 36 am layer of the tested inventive or comparative compound was deposited on the emitting layer together with 50 wt. % D1 or D2 or with 5 wt. % Mg as ETL. Subsequently a layer of aluminium with a thickness of 100 nm was deposited.

The observed voltages and quantum efficiencies at the current density 10 mA/cm$^2$ are reported in the Table 1.

When comparing all data in the Table 1, it becomes clear that the semiconducting materials of the present invention represent an inventive alternative for known semiconducting materials.

The features disclosed in the foregoing description, in the claims and in the accompanying drawings may both separately and in any combination be material for realizing the invention in diverse forms thereof.

Used Acronyms and Abbreviations

CGL charge generating layer
CV cyclovoltammetry
DCM dichloromethane
DSC differential scanning calorimetry
DFT density functional theory
DME 1,2-dimethoxyethane
EA electron affinity
EE ethylester (ethyl acetate)
EI electron impact (direct inlet mass spectroscopy)
EIL electron injection layer
ESI electrospray ionization (mass spectroscopy)
ETL electron transporting layer
ETM electron transporting matrix
Fc$^+$/Fc ferrocenium/ferrocene reference system
GC gas chromatography
HIL hole injection layer
HPLC high performance liquid chromatography
HOMO highest occupied molecular orbital
HTL hole transporting layer
HTM hole transporting matrix
IP ionisation potential
IPES inverted photoelectron spectroscopy
ITO indium tin oxide
LDA lithium diisopropyl amide
LUMO lowest unoccupied molecular orbital
MS mass spectroscopy
NMR nuclear magnetic resonance
OLED organic light emitting diode
RT room temperature
SPS solvent purification system
TGA thermogravimetry thermal analysis
THF tetrahydrofuran
TLC thin layer chromatography
UPS ultraviolet photoelectron spectroscopy
UV spectroscopy in the ultra violet/visible range of light spectrum
VTE vacuum thermal evaporation
eq chemical equivalent
mol. % molar percent
vol. % volume percent
wt. % weight (mass) percent
mp melting point

We claim:
1. Semiconducting material comprising an electrical dopant and
an electron transport matrix compound comprising at least one electron transporting structural moiety and at least one polar structural moiety, the at least one polar structural moiety being selected
a) from a structural moiety consisting of one atom of 15$^{th}$ group of the Periodic Table and one atom of 16$^{th}$ group of the Periodic Table linked together by a covalent bond, or
b) from a heteroaryl selected from pyridine-4-yl, quinoline-4-yl, and 1,3,5-triazine-2-yl, or
c) from a benzimidazolyl moiety having formula (Ia) or (Ib)

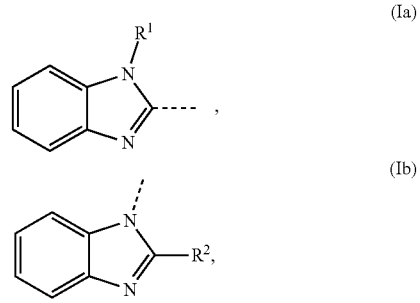

wherein the dashed line represents the bond attaching the benzimidazolyl moiety of formula (Ia) or (Ib) to other structural moieties of the molecule, R$^1$ and R$^2$ are selected from
(i) C$_1$-C$_{24}$ alkyl,
(ii) C$_3$-C$_{24}$ cycloalkyl,
(iii) C$_6$-C$_{24}$ aryl,
(iv) C$_7$-C$_{24}$ arylalkyl,
(v) C$_3$-C$_{24}$ heteroalkyl or C$_4$-C$_{24}$ heterocycloalkyl or C$_8$-C$_{24}$ aryl-heteroalkyl each comprising at least one heteroatom selected from Si and Ge,
(vi) C$_2$-C$_{24}$ heteroalkyl or C$_3$-C$_{24}$ heterocycloalkyl or C$_7$-C$_{24}$ aryl-heteroalkyl each comprising at least one heteroatom selected from B and P, or
(vii) C$_2$-C$_{24}$ heteroaryl comprising up to 4 heteroatoms independently selected from N, O and S; wherein
the at least one electron transporting structural moiety comprises a benzo-naphthofurane structural moiety, with the proviso that the case that the benzo-naphthofurane structural moiety has the structure (IIa)

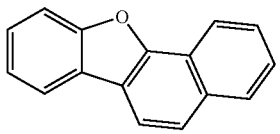
(IIa)

and the polar structural moiety has the structure (Ib) is excluded.

2. Semiconducting material according to claim 1, wherein the benzo-naphthofurane structural moiety and the polar structural moiety are mutually connected by an arylene or heteroarylene linker.

3. Semiconducting material according to claim 2, wherein the arylene linker is a phenylene.

4. Semiconducting material according to claim 1, wherein the benzo-naphthofurane structural moiety is a dinaphtho-furane structural moiety.

5. Semiconducting material according to claim 4, wherein the dinaphthofurane structural moiety has the structure according to formula (II)

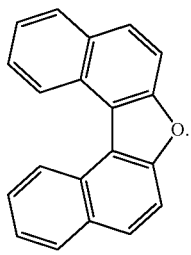
(II)

6. Semiconducting material according to claim 1, wherein the polar structural moiety is a phosphine oxide group directly attached to structural moieties which may be independently selected from arene and heteroarene structural moieties.

7. Semiconducting material according to claim 1, wherein the electrical dopant is selected from a metal in a substantially elemental form and/or from a metal salt.

8. Electronic device comprising between two electrodes at least one substantially organic layer comprising the semiconducting material according to claim 1.

9. Compound comprising at least one structural moiety having formula (II)

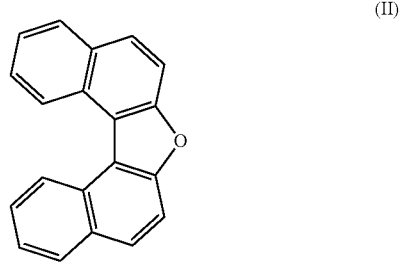 [SMILES: c1ccc2c(c1)ccc1oc3ccc4ccccc4c3c12]
(II)

and at least one polar structural moiety selected as 1,3,5-triazine-2-yl.

* * * * *